(12) United States Patent
MacLeod et al.

(10) Patent No.: US 9,775,802 B2
(45) Date of Patent: Oct. 3, 2017

(54) METHOD FOR PREPARING SUSPENSIONS OF LOW-SOLUBILITY MATERIALS

(71) Applicant: Bausch & Lomb Incorporated, Rochester, NY (US)

(72) Inventors: Steven K. MacLeod, Henrietta, NY (US); Daniel J. Stein, Rochester, NY (US); James Donald Hayes, Tampa, FL (US); Donald L. Herber, Tampa, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 14/519,776

(22) Filed: Oct. 21, 2014

(65) Prior Publication Data

US 2015/0038439 A1 Feb. 5, 2015

Related U.S. Application Data

(63) Continuation-in-part of application No. 12/714,577, filed on Mar. 1, 2010, now abandoned.

(60) Provisional application No. 61/162,694, filed on Mar. 24, 2009.

(51) Int. Cl.
| | | |
|---|---|---|
| *A61K 47/32* | (2006.01) | |
| *A61K 9/10* | (2006.01) | |
| *A61K 31/196* | (2006.01) | |
| *A61K 31/4709* | (2006.01) | |
| *A61K 31/55* | (2006.01) | |
| *A61K 31/573* | (2006.01) | |
| *A61K 31/7052* | (2006.01) | |
| *A61K 9/00* | (2006.01) | |

(52) U.S. Cl.
CPC .............. *A61K 9/10* (2013.01); *A61K 9/0048* (2013.01); *A61K 31/196* (2013.01); *A61K 31/4709* (2013.01); *A61K 31/55* (2013.01); *A61K 31/573* (2013.01); *A61K 31/7052* (2013.01)

(58) Field of Classification Search
CPC .... A61K 2300/00; A61K 45/06; A61K 38/00; A61K 39/3955; A61K 2039/505; A61K 31/7115; A61K 38/17; A61K 38/177; A61K 38/45; A61K 48/0033; A61K 48/005; A61K 48/0066; A61K 9/1271; A61K 31/198
See application file for complete search history.

(56) References Cited

U.S. PATENT DOCUMENTS

| | | |
|---|---|---|
| 5,811,417 A | 9/1998 | Bellmann |
| 6,379,692 B1 | 4/2002 | Rao .............................. 424/427 |
| 6,682,761 B2 | 1/2004 | Pace et al. .................... 424/489 |
| 8,486,993 B2 | 7/2013 | Holm |
| 2002/0187193 A1 | 12/2002 | Roy et al. |
| 2003/0232020 A1 | 12/2003 | York et al. ...................... 424/46 |
| 2005/0250804 A1 | 11/2005 | Kannan et al. ............... 514/291 |
| 2008/0233183 A1 | 9/2008 | McCook et al. ............. 424/450 |
| 2008/0260837 A1 | 10/2008 | Namburi et al. ............. 424/488 |
| 2011/0201639 A1 | 8/2011 | Skak et al. |

FOREIGN PATENT DOCUMENTS

| | | |
|---|---|---|
| CN | 1460013 A | 12/2003 |
| EP | 1663217 B1 | 7/2010 |
| GB | 2328872 A | 3/1999 |
| JP | 8295622 A | 11/1996 |
| JP | H10500684 A | 1/1998 |
| JP | H11240838 A | 9/1999 |
| JP | 2004529199 A | 9/2004 |
| JP | 2008519759 A | 6/2008 |
| WO | WO 99/15165 A1 | 4/1999 |
| WO | WO 02/11683 A1 | 2/2002 |

OTHER PUBLICATIONS

Savjani, Ketan T. et al. "Drug Solubility: Importance and Enhancement Techniques", Review Article, International Scholarly Research Network: ISRN Pharmaceutics; vol. 2012, Article ID 195727, doi: 10.5402/2012/195727, published 2012. pp. 1-10.*
Martindale, "The Complete Drug Reference," 34th ed., 2005, (p. 1411-1416).
The Merck Index, "Tacrolimus," 1996, 12 ed., (p. 9199).
S. Babic et al., Trends in Analytical Chem., 26(1): 1043-61 (2007).
R. Aura et al., Acta Medica Marisiensis, 60(3): 109-15 (2014).
Bayer press release: FDA approves Avelox™ (moxifloxacin hydrochloride), An Important New Treatment For Respiratory Illnesses (12 pages) Dec. 13, 1999 (www.drugbank.ca/drugs/DB00218).
BusinessWire: "InSite Vision Announces FDA Approval of New Ophthalmic Product Enabled by InSite's DuraSite® Technology" (15 pages) Jun. 2, 2009 (www.drugbank.ca/drugs/DB06771).
Remington: "Nanionic Agents" The Science and Practice of Pharmacy, 21st ed. ©2012 (p. 291).
Swarbrick et al.: "Coarse Dispersions" © Pharmaceutical Press 2012, Chapter 22 (p. 371-391).
Astellas Pharma US, Inc.: "Protopic—tacrolimus ointment; Prescribing Information" 16 pages, Revised Nov. 2011.
Lubrizol—Pharmaceutical Bulletin 21: "Formulating Semisolid Products" 7 pages, May 31, 2011.
Kino et al.: "A Novel Immunosuppressant Isolated From A Streptomyces" 10 pages, Sep. 1987.

* cited by examiner

*Primary Examiner* — Audrea Buckley
(74) *Attorney, Agent, or Firm* — John E. Thomas

(57) ABSTRACT

A process for producing a pharmaceutical suspension that comprises an active pharmaceutical ingredient ("API") having low solubility, the process comprises: (a) preparing a first solution comprising a carboxy-containing vinyl polymer and a solvent; and (b) adding a compound of the API to said first solution under conditions of high-shear mixing for a time from about 5 minutes to about 5 hours, said compound being soluble in said solvent, thereby producing a suspension of particles of said API in a composition comprising said carboxy-containing vinyl polymer; wherein a concentration of said API in said suspension is higher than a solubility of said API in said solvent. The present invention also provides a suspension produced by such process.

9 Claims, 3 Drawing Sheets

METHOD FOR PREPARING SUSPENSIONS OF LOW-SOLUBILITY MATERIALS

CROSS REFERENCE

This application is a continuation-in-part application, and claims the benefit, of patent application having Ser. No. 12/714,577, filed Mar. 1, 2010, which claims the benefit of provisional patent application having Ser. No. 61/162,694, filed Mar. 24, 2009. The contents of said prior-filed applications are incorporated by reference herein in their entirety.

BACKGROUND

The present invention relates to a method for preparing suspensions of materials having low solubility. The present invention also relates to suspensions prepared by such a method.

In many applications, it is often desired to deliver a large amount of a material to a target. For example, in the pharmaceutical art, a sufficiently high dose of an active ingredient delivered to a target tissue is typically required to provide an effective treatment of a disorder. Such a sufficient dose may be achieved through a sufficiently high concentration of the active ingredient in the formulation for a short time or, alternatively, through sustained delivery of a lower concentration for an extended time.

Many active pharmaceutical ingredients ("APIs") have low solubility in commonly used media such as aqueous compositions. Therefore, such APIs are often formulated into suspensions containing particles thereof for sustained delivery and achievement of sufficiently effective doses.

Formulating suspension of low-solubility materials presents many challenges. For example, in one aspect, the efficacy of a pharmaceutical suspension is related to the particle size of the API. Typically, better pharmaceutical suspensions are achieved with smaller particles and more uniform size because of higher and more consistent release rate. However, pulverization of solid APIs to obtain small particles may lead to excessive local temperature increase and agglomeration.

Poor physical stability is another challenge. Larger particles of a population having wide particle size distribution can settle out of the suspension and are not easily resuspended, leading to undesirable variable drug dosages when administered to a patient.

Therefore, there is a continued need to provide improved suspensions containing APIs having low solubility. It is also desirable to provide methods for preparing improved suspensions that, avoid at least some of the problems of prior-art methods.

SUMMARY

In general, the present invention provides a method for preparing suspensions that comprise a material having low solubility and suspensions resulting from such a method.

In one aspect, the present invention provides a method for preparing a pharmaceutical suspension that comprises an API having low solubility and suspensions resulting from such a method.

In another aspect, the present invention provides a method for preparing an ophthalmic suspension that comprises an ophthalmic API having low solubility and suspensions resulting from such a method.

In still another aspect, an ophthalmic suspension of the present invention provides increased bioavailability of such an ophthalmic API in an ocular tissue of a subject.

In yet another aspect, a method of the present invention comprises: (a) preparing a first solution comprising a carboxy-containing vinyl polymer and a solvent; and (b) adding a compound of an API to said first solution under conditions of high-shear mixing for a time from about 5 minutes to about 5 hours, said compound being soluble in said solvent, thereby producing a suspension of particles of said API in a composition comprising said carboxy-containing vinyl polymer; wherein a concentration of said API in said suspension is higher than a solubility of said API in said solvent.

In a further aspect, said API is an ophthalmic API.

In still another aspect, said suspension is a topically administrable composition.

Other features and advantages of the present invention will become apparent from the following detailed description and claims.

BRIEF DESCRIPTION OF THE DRAWINGS

The numbers in the legends of FIGS. 1-3 indicate the lot numbers.

DETAILED DESCRIPTION

Figure 1:
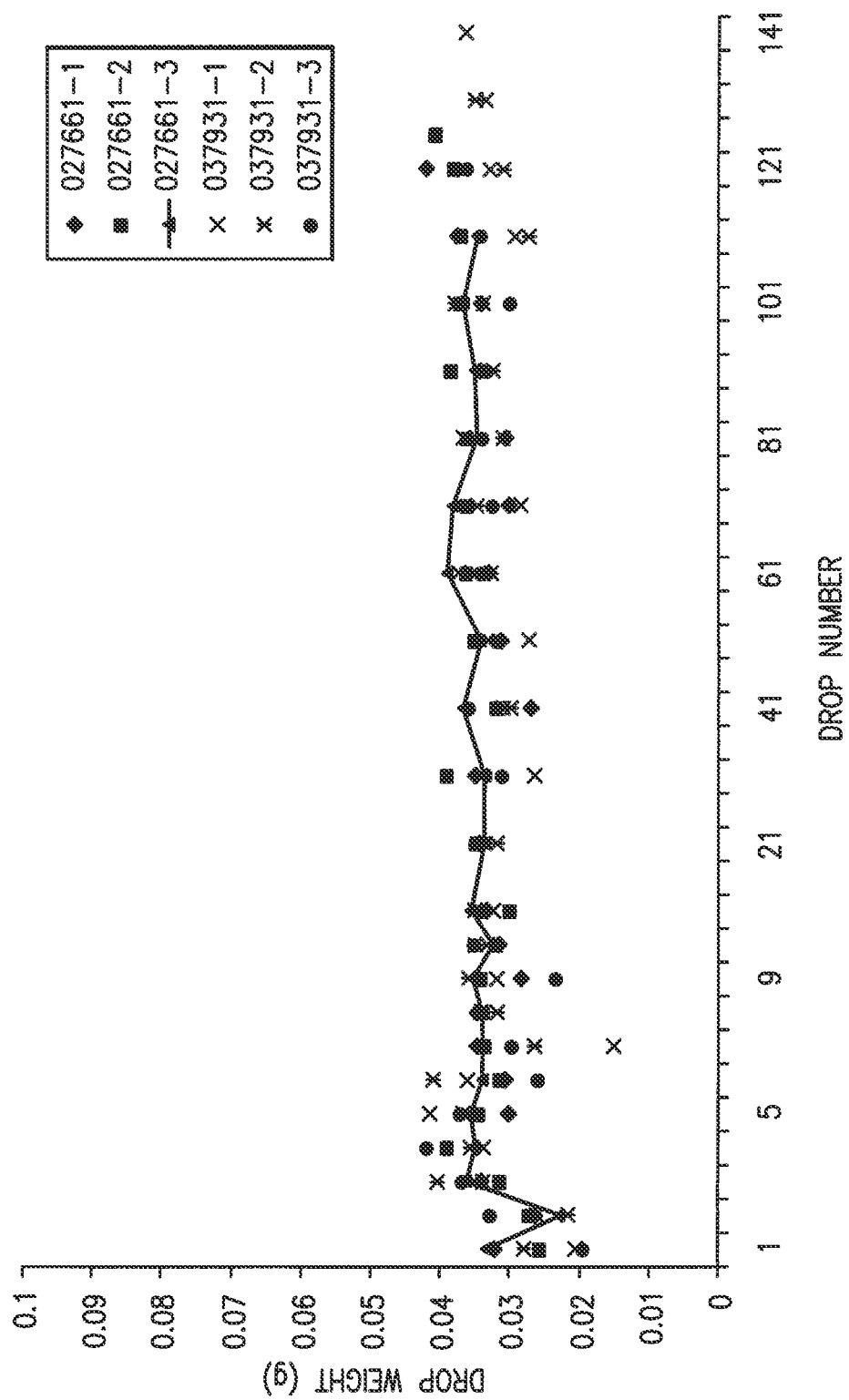
FIG. 1 shows the consistency of drop weights of a besifloxacin suspension produced by a method of the present invention.

In general, the present invention provides a method for preparing suspensions that comprise a material having low solubility and suspensions resulting from such a method.

As used herein, "low solubility" means solubility of 0.5 mg/mL or less in water at about 25° C. and pH of about 7.

In one aspect, the present invention provides a method for preparing suspensions that comprise an API having low solubility and suspensions resulting from such a method.

In another aspect, a method of the present invention comprises: (a) preparing a first solution comprising a carboxy-containing vinyl polymer and a solvent; and (b) adding a compound of an API to said first solution under conditions of high-shear mixing for a time from about 5 minutes to about 5 hours, said compound being soluble in said solvent, thereby producing a suspension of particles of said API in a composition comprising said carboxy-containing vinyl polymer; wherein a concentration of said API in said suspension is higher than a solubility of said API in said solvent. In one embodiment, said compound comprises a salt, (e.g., pharmaceutically acceptable salt) of said API. In another embodiment, said compound comprises a hydrate of said API. In still another embodiment, said compound comprises a solvate of said API.

In still another aspect, the solvent comprises water.

In yet another aspect, the particles of the API in the suspension have a mean particle diameter of not greater than about 4 μm (or alternatively, in the range from about 1 to about 4 μm) and a $D_{90}$ of not greater than about 7 μm (or alternatively, in the range from about 3 to about 7 μm), wherein $D_{90}$ means the diameter which is greater than those of particles that constitute 90 percent, of the volume of all particles. Such particle, diameter is determined by light diffraction measurement according to the USP (US Pharmacopeia) <429> standard.

In still another aspect, the particles of the API in the suspension have a mean particle diameter of about 4 μm (or alternatively, about 3 μm, or about 2 μm), and a $D_{90}$ of about 7 μm (alternatively, about 5 μm, or about 4 μm, or about 3 μm).

In a further aspect, the particles of the API in the suspension can have a $D_{99}$ of about 5 μm (or alternatively, about 4 μm), wherein $D_{99}$ means the diameter which is greater than those of particles that constitute 99 percent, of the volume of ail particles.

In still another aspect, the suspension has a viscosity in the range from about 500 to about 3000 cp (or mPa·s). Alternatively, the suspension has a viscosity in the range from about 700 to about 2000 cp (or from about 900 to about 1700 cp, or from about 1000 to about 1600 cp, or from about 1600 to about 3000 cp, or from about 1000 to about 2000 cp).

In yet another aspect, the conditions of high-shear mixing include rotational speed in the range from about 500 to about 2000 rpm. Alternatively, the conditions of high-shear mixing include rotational speed in the range from about 600 to about 1800 rpm, or from about 600 to about 1600 rpm, or from about 700 to about 1500 rpm, or from about 700 to about 1400 rpm, or from about 900 to about 1500 rpm, or from about 1000 to about 1600 rpm.

In yet another aspect, the conditions of high-shear mixing include rotational speed in the range from 500 to 2000 rpm. Alternatively, the conditions of high-shear mixing include rotational speed in the range from 600 to 1800 rpm, or from 600 to 1600 rpm, or from 700 to 1500 rpm, or from 700 to 1400 rpm, or from 900 to 1500 rpm, or from 1000 to 1600 rpm.

In a further aspect, the carboxy-containing vinyl polymer comprises a polyacrylic acid polymer.

In one embodiment, the carboxy-containing vinyl polymer is a crosslinked or lightly crosslinked polyacrylic acid polymer comprising an amount of crosslinking agent units less than 10 percent (or alternatively, less than about 5 percent) of the total weight of the polymer. In another embodiment, the carboxy-containing vinyl polymer can be selected from polymers known in the art as polycarbophil (such as Noveon® AA-1), Carbopol® (such as Carbopol® 934, 940, or 941), and Pemulen™ (such as Pemulen™ TR-1 or TR-2).

In another aspect, the amount of the carboxy-containing vinyl polymer is in the range from about 0.01 to about 10 percent by weight of the final suspension. Alternatively, the amount of the carboxy-containing vinyl polymer is in the range from about 0.01 to about 5 (or from about 0.01 to about 2, or from about 0.01 to about 1, or from about 0.05 to about 1, or from about 0.1 to about 1, or from about 0.1 to about 2, or from about 0.5 to about 2, or from about 1 to about 2) percent by weight of the final suspension.

In another aspect of the present invention, the API can comprise a therapeutic agent such as anti-inflammatory agents, antibiotics, immunosuppressive agents, antiviral agents, antifungal agents, antiprotozoal agents, combinations thereof, or mixtures thereof. Non-limiting examples of anti-inflammatory agents include glucocorticosteroids (e.g., for short-term treatment) and non-steroidal anti-inflammatory drugs ("NSAIDs").

Non-limiting examples of the glucocorticosteroids are: 21-acetoxypregnenolone, alcfometasone, algestone, amcinonide, beclomethasone, betamethasone, budesonide, chloroprednisone, clobetasol, clobetasone, clocortolone, cloprednol, corticoslerone, cortisone, cortivazol, defiazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcirtonide, halobetasol propionate, halometasone, halopredone acetate, hydrocortarnate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, their physiologically acceptable salts, derivatives thereof, combinations thereof, and mixtures thereof. In one embodiment, the therapeutic agent is selected from the group consisting of difluprednate, loteprednol etabonate, prednisolone, combinations thereof, and mixtures thereof.

Non-limiting examples of the NSAIDs are: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), aryiacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazoiac, metiazinic acicl, mofezolac, oxametactne, pirazolac, proglumetacin, sulindac, tiaramide, tolmetin, tropesin, zomepirac), arylbutyric acid derivatives (e.g., bumadizon, butibufen, fenbufen, xenbucin), aryicarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosai, gentisic acid, glycol salicylate, imidazole salicylate, lysine acetylsalicylate, mesalamine, morphoiine salicylate, 1-naphthyl salicylate, olsalazine, parsalmide, phenyl acetylsalicylate, phenyl salicylate, salacetamide, salicylamide o-acetic acid, salicylsulfuric acid, saisalate, sulfasalazine), thiazinecarboxamides (e.g., ampiroxicam, droxicam, isoxicam, lornoxicam, piroxicam, tenoxicam), ε-acetamidocaproic acid, S-(5'-adenosyl)-L-methionine, 3-amino-4-hydroxybutyric acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, their physiologically acceptable salts, combinations thereof, and mixtures thereof.

Non-limiting examples of antibiotics include doxorubicin; aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin SV, rifapentine, rifaximin), β-lactams (e.g., carbacephems (e.g., loracarbef)), carbapenems (e.g., biapenem, imtpenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforamide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefininox, cefotetan, cefoxitin), monobactams (e.g., aztreonam, carumonam, tigemonam), oxacephems, flomoxef, moxalactam), penicillins (e.g., anidinociliin, amdinocillin pivoxil, amoxicillin, ampicillin, apaicillin, aspoxicillin, azidocillin, azlocillin, bacampiciliin, benzylpenicillinic acid, benzyipeniciilin sodium, carbenicillin, carindacillin, clometocillin, cloxaciilin, cyclacillin, dicloxacillin, epiciilin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), Hncosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin S, gramicidin(s), mikamycin, polymyxin, pristinamycin, ristocetin, teicoplanin, thiostrepton, tuberactinomycin, tyrocidine, tyrothricin, vancomycin, viomyein, virginiamycin, zinc bacitracin), tetracyclines (e.g., apicycline, chlortetracycline, clomocycline, demeclocycline, doxycycline, guamecyciine, lymecycline, meclocyciine, methacycline, minocycline, oxytetracycline, penimepicycline, pipacycline, rolitetracycline, sancycline, tetracycline), and others (e.g., cycloserine, mupirocin, tuberin).

Other examples of antibiotics are the synthetic antibacterials, such as 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinoi, nitrofurantoin), quinolones and analogs (e.g., cinoxacin, ciprofloxacin, clinafioxacin, difloxacin, enoxacin, fleroxacin, flumequine, grepafloxacin, lomefloxaein, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-B, chloramine-T, dichloramine T, $n^2$-formylsulfisomidine, $n^2$-β-D-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, suifaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene citrate, methenamine hippurate, methenamine mandelate, methenamine subsalicylate, nitroxoline, taurolidine, xibomol).

Non-limiting examples of immunosuppressive agents include dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur), fluocinolone, triaminolone, anecortave acetate, fiuorometholone, medrysone, and prednisolone.

Non-limiting examples of antifungal agents include polyenes (e.g., amphotericin B, candicidin, dermostatin, filipin, fungichromin, hachimycin, hamycin, lucensomycin, mepartricin, natamycin, nystatin, pecilocin, perimycin), azaserine, griseofuivin, oligomycins, neomycin undecylenate, pyiroinitrin, siccanin, tubercidin, viridin, ailylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazoie, isoeonazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole), acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, haiethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate.

Non-limiting examples of antiviral agents include acyclovir, carbovir, famciclovir, ganciclovir, penciclovir, and zidovudine.

Non-limiting examples of antiprotozoal agents include pentamidine isethionate, quinine, chloroquine, and mefloquine.

In still another aspect, the first solution can further comprise one or more additional materials, such as chelating agents, tonicity-adjusting agents, pH-adjusting agents, buffers, antioxidants, surfactants, or additional viscosity-adjusting agents. The final suspension can also include a preservative for multi-dose applications.

Non-limiting examples of physiologically acceptable buffers include phosphate buffer; a Tris-HCl buffer (comprising tris(hydroxymethyl)aminomethane and HCl); buffers based on HEPES (N-{2-hydroxyethyl}peperazine-N'-{2-ethanesulfonic acid; BES (N,N-bis{2-hydroxyethyl}2-aminoethanesulfonic acid); MOPS (3-{N-morpholino}propanesulfonic acid); TES (N-tris{hydroxymethyl}-methyl-2-aminoethanesulfonic acid); MOBS (4-{N-morpholino}butanesulfonic acid); DIPSO (3-(N,N-bis{2-hydroxyethyl}amino)-2-hydroxypropane)); and TAPSO (2-hydroxy-3-{tris(hydroxymethyl)methylamino}-1-propanesulfonic acid)).

Non-limiting examples of anti-oxidants include ascorbic acid (vitamin C) and its salts and esters; tocopherols (such as α-tocopherol) and tocotrienols (vitamin E), and their salts and esters (such as vitamin E TGPS (D-α-tocopheryl polyethylene glycol 1000 succinate)); glutathione; lipoic acid; uric acid: butylated hydroxyanisole ("BHA"); butylated hydroxytoluene ("BHT"); tertiary butylhydroquinone ("TBHQ"); and polyphenolic anti-oxidants (such as gallic acid, cinnanmic acid, flavonoids, and their salts, esters, and derivatives). In some embodiments, the anti-oxidant comprises ascorbic acid (vitamin C) and its salts and esters; tocopherols (such as α-tocopherol) and tocotrienols (vitamin E), and their salts and esters; or BHA.

In still another embodiment, the amount of an anti-oxidant in a pharmaceutical formulation of the present invention is in the range from about 0.0001 to about 5 percent by weight of the formulation. Alternatively, the amount of an anti-oxidant is in the range from about 0.001 to about 3 percent, or from about 0.001 to about 1 percent, or from greater than about 0.01 to about 2 percent, or from greater than about 0.01 to about 1 percent, or from greater than about 0.01 to about 0.7 percent, or from greater than about 0.01 to about 0.5 percent, or from greater than about 0.01 to about 0.2 percent, or from greater than about 0.01 to about 0.1 percent, or from greater than about 0.01 to about 0.07 percent, or from greater than about 0.01 to about 0.05 percent, or from greater than about 0.05 to about 0.15 percent, or from greater than about 0.03 to about 0.15 percent by weight of the solution, or from greater than about 0.1 to about 1 percent, or from greater than about 0.1 to about 0.7 percent, or from greater than about 0.1 to about 0.5 percent, or from greater than about 0.1 to about 0.2 percent, or from greater than about 0.1 to about 0.15 percent.

Non-limiting chelating agents include compounds having Formula I, II, or III.

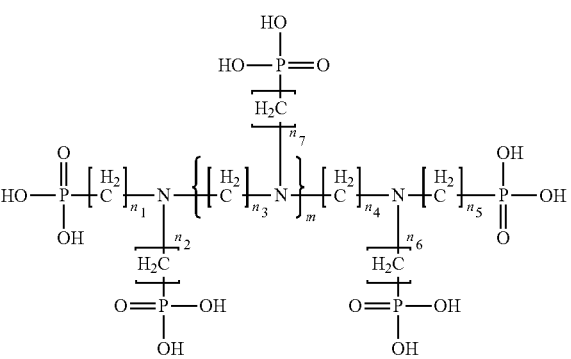

(I)

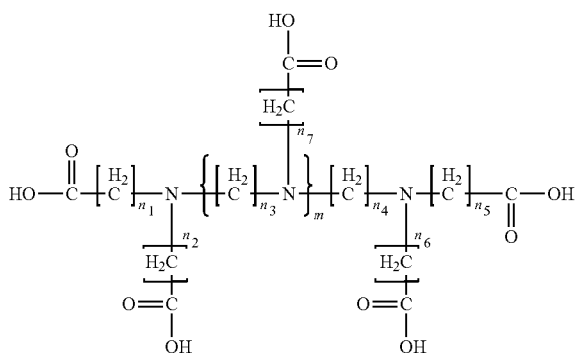

(II)

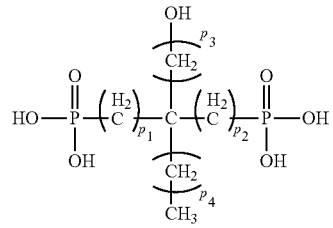

(III)

wherein $n_1$, $n_2$, $n_3$, $n_4$, $n_5$, $n_6$, and $n_7$ are integers independently in the range from 1 to 4, inclusive; m is an integer in the range from 1 to 3, inclusive; $p_1$, $p_2$, $p_3$, and $p_4$ are independently selected from 0 and integers in the range from 1 to 4, inclusive.

In some embodiments, the chelating agent comprises a compound selected from the group consisting of ethylenediaminetetraacetic acid ("EDTA"), dieihyienetriaminepentakis(methylphosphonic acid), etidronic acid, pharmaceutically acceptable salts thereof, and mixtures thereof.

In some other embodiments, the chelating agent comprises tetrasodiuni salt of etidronic acid (also known as "HAP", which is available as 30% solution).

In still some other embodiments, the chelating agent comprises EDTA sodium salt (commonly known as edetate disodium).

Tonicity-adjusting agents may be added to adjust the final tonicity of the suspension. Such tonicity-adjusting agents are well known to those of skill in the art and include, but are not limited to, mannitol, sorbitol, dextrose, sucrose, urea, propylene glycol, and glycerin. Also, various salts, including halide salts of a monovalent cation (e.g., NaCl or KCl) can be utilized.

The tonicity-adjusting agent, when present, can be in a concentration ranging from about 0.03 to about 10, or from about 0.01 to about 7, or from about 0.01 to about 5, or from about 0.1 to about 2, or from about 0.1 to about 1 percent, by weight. In some embodiments where a tonicity adjusting agent is present the solution can contain a single agent or a combination of different tonicity adjusting agents. Typically, the tonicity of a formulation of the present invention is in the range from about 200 to 400 mOsm/kg. Alternatively, the tonicity of a formulation of the present invention is in the range from about 220 to 400 mOsm/kg, or from about 220 to 350 mOsm/kg, or from about 220 to 300 mOsm/kg, or from about 250 to 350 mOsm/kg, or from about 250 to 300 mOsm/kg, or from about 240 to 280 mOsm/kg.

Ophthalmic formulations of the present invention also can comprise one or more surfactants. Suitable surfactants can include cationic, anionic, non-ionic or amphoteric surfactants. Preferred surfactants are neutral or nonionic surfactants. Non-limiting examples of surfactants suitable for a formulation of the present invention include polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). Such compounds are delineated in Martindale, 34th ed., pp 1411-1416 (Martindaie, "The Complete Drug Reference," S. C. Sweetman (Ed.), Pharmaceutical Press, London, 2005) and in Remington, "The Science and Practice of Pharmacy," 21$^{st}$ Ed., pp 293 and the contents of chapter 22, Lippincott Williams & Wilkins, New York, 2006. The concentration of a non-ionic surfactant, when present, in a composition of the present invention can be in the range from about 0.001 to about 5 weight percent (or alternatively, from about 0.01 to about 4, or from about 0.01 to about 2, or from about 0.01 to about 1 weight percent).

In some embodiments, the ophthalmic formulations of this invention can optionally include other viscosity-adjusting agents. Suitable viscosity-adjusting agents for administration to an eye are well known to those of skill in the art. Non-ionic polysaccharides such as cellulose derivatives are commonly used to increase viscosity, and as such, can offer other advantages. Specific cellulose derivatives (ionic and non-ionic) include, but are not limited to hydroxypropyl methyl cellulose, carboxymethyl cellulose, methyl cellulose, or hydroxyethyl cellulose. Viscosity may be adjusted to be in the range from about 500 to about 3000 centipoises (or mPa·s). A suspension of the present invention can be easily dispensed in the eye in the form of an eye drop. It should be understood, however, that the present method may also be employed to produce formulations having even higher viscosity, for ophthalmic or non-ophthalmic uses.

In addition to those classes of ingredients disclosed above, a pharmaceutical formulation, such as an ophthalmic solution, of the present invention can further comprise one or more other ingredients, such as vitamins (other than those disclose hereinabove), or other ingredients that provide added health benefits to the users.

In another embodiment, a suspension of the present invention can comprise one or more preservatives selected from the group consisting of benzalkonium chloride ("BAK"), polyquaternium-1, polyquaternium-10, other polyquaternium compounds, cationic organic nitrogen-containing compounds other than the foregoing compounds, alcohols, stabilized oxychloro complex (an equilibrium mixture of oxychloro species), hydrogen peroxide, and compounds that can generate hydrogen peroxide. In still some other embodiments, a preservative, is present at a concentration from about 0.001 to about 0.2 percent, or from about 0.001 to about 0.1 percent, or from about 0.001 to about 0.05 percent, or from about 0.001 to about 0.01 percent by weight of the total formulation.

Formulation Compounding Procedure

In one aspect, a method for preparing a suspension that comprises a material having low solubility comprises the steps of: (a) adding a predetermined amount of a solvent (such as water or purified water) into a vessel, which is equipped with an operating high-shear mixing implement; (b) sequentially adding predetermined amounts of one or more other desired ingredients other than the material having low solubility and a compound thereof into the vessel while mixing continues; (c) adding a desired amount of a carboxy-containing vinyl polymer into the vessel while mixing continues until such polymer is substantially completely dissolved to produce a first solution; (d) adjusting pH of the first solution to a predetermined pH value; and (e) adding a predetermined amount of a compound of the material having low solubility into the first solution while mixing continues under conditions of high-shear mixing to produce the suspension.

In one aspect, the compound of the material having low solubility is added into the first solution as a neat, solid material.

In one embodiment, the method further comprises adjusting the pH of the formulation or composition to a desired pH value. In another embodiment, the desired pH value is in the range from about 5 to about 8 (or alternatively, from about 6 to about 8, or from about 6.5 to about 7.5, or from about 6.0 to about 6.8, or from about 6.5 to about 6.8, or from about 6.3 to about 6.7, or from about 6.5 to about 6.7).

In one aspect, the present method comprises adjusting and maintaining the pH of the formulation or composition within one of the above pH ranges throughout the practice of the method.

In another aspect, the temperature of the formulation or composition is maintained in the range of 20-30° C. throughout the practice of the method.

In another embodiment, the method further comprises adding a preservative to the suspension while mixing continues, and sterilizing the resulting suspension.

In one aspect, the conditions of high-shear mixing include rotational speed in the range from about 500 to about 2000 rpm. Alternatively, the conditions of high-shear mixing include rotational speed in the range from about 600 to about 1800 rpm, or from about 600 to about 1600 rpm, or from about 700 to about 1500 rpm, or from about 700 to about 1400 rpm, or from about 900 to about 1500 rpm, or from about 1000 to about 1600 rpm.

In another aspect, the conditions of high-shear mixing include rotational speed in the range from 500 to 2000 rpm. Alternatively, the conditions of high-shear mixing include rotational speed in the range from 600 to 1800 rpm, or from 600 to 1600 rpm, or from 700 to 1500 rpm, or from 700 to 1400 rpm, or from 900 to 1500 rpm, or from 1000 to 1600 rpm.

In still another aspect, the mixing under conditions of high-shear mixing continues for a time from about 5 minutes to about 5 hours.

Although the inventors do not wish to be bound by any particular theory, they believed that the conditions of high-shear mixing result in continuous break-up of particles as they are being formed from a supersaturated composition, thus producing advantageous particle size and distribution. The method of the present invention advantageously avoids the excessive temperature, rise and agglomeration of the resulting particles that are produced by other prior-art methods. In addition, the method of the present invention is advantageously employed with temperature-sensitive APIs.

EXAMPLE 1

Preparing a Suspension Comprising Particles of Besifloxacin (Compound Having Formula IV)

(IV)

An amount of water of about 75 percent of the desired weight of the batch was added to a clean, jacketed, suitably sized stainless steel vessel ("the first vessel") equipped with a combination of counter-rotating stirrer and scrapper, a homogenizer, and an auxiliary mixing impeller. About two liters of water were set aside for rinsing ingredient containers after addition.

Impeller mixing was initiated at 500-600 rpm and the homogenizer at 650-1400 rpm. The temperature was adjusted to, and maintained at, 20-30° C.

The following ingredients were added slowly and mixed until dissolved: edetate disodium (0.1 percent of the final batch weight), sodium chloride (0.5 percent of the final batch weight).

An amount of Polycarbophil equal to about 8.5 weight percent of the final batch weight was slowly added to the vessel. The mixture was mixed for not less than 30 minutes to hydrate the Polycarbophil. The temperature of this mixture was maintained at 20-30° C. Note that the unadjusted pH of an aqueous solution of a carboxyvinyl polymer, such as polycarbophil (or carbomer or Pemulen™), is in the acidic range.

An amount of mannitol equal to about 1 percent of the final batch weight was added to the mixture. Mixing continued for 5-10 minutes while the temperature was maintained at 20-30° C.

About 10 percent of the final batch weight was added to another clean, suitably sized stainless steel vessel ("the second vessel") equipped with an impeller mixer. Mixing was initiated at 300-600 rpm and the temperature was adjusted to, and maintained at, 20-30° C. An amount of Poloxamer 407 equal to about 0.1 percent of the final batch weight was added to this vessel while mixing continued for not less than 10 minutes. The solution of Poloxamer was slowly added to the contents of the first vessel. The stirrer/scrapper combination was initiated at 5-40 rpm. Mixing continued for not less than 10 minutes while the temperature was maintained at 20-30° C.

An amount of NaOH was added slowly to the contents of the first vessel to adjust the pH to 6.5-6.7.

The homogenizer mixing speed was set to 1400-1500 rpm, and mixing continued for not less than 30 minutes to achieve a smooth gel while the temperature was maintained at, 20-30° C.

The pH of the mixture was checked again and adjusted, if necessary, to 6.5-6.7 with additional NaOH solution. The pH of the mixture was maintained at 6.5-6.7. Mixing continued for 10-30 minutes after each adjustment, and the temperature was maintained at 20-30° C.

An amount of the hydrochloride addition salt of besifloxacin equal to 0.6 percent of the final batch weight was added slowly to the first vessel while the homogenizer continued to operate at 1400-1500 rpm and mixing continued for not less than 30 minutes while the temperature was maintained at 20-30° C.

In one embodiment, the hydrochloride addition salt of besifloxacin was added as a neat, solid material. In another embodiment, the hydrochloride addition salt of besifloxacin was added as a component of a mixture, which may be a liquid, with one or more additional pharmaceutically acceptable excipients. However, the pH of such a mixture, if it is a liquid, is kept in the acidic pH range.

The unused amount of water that was reserved for rinsing ingredient containers was added to the batch. The pH was checked and adjusted to, and maintained at, 6.3-6.7 (preferably, 6.5-6.7) with additional NaOH solution. Mixing continued for 10-30 minutes after each pH adjustment while the temperature was maintained at 20-30° C.

The bulk of the batch was transferred from the first vessel through a stainless steel 150 mesh filter strainer into an aseptic pressure vessel equipped with a stirrer/scrapper. The first vessel and transfer lines were rinsed with a small amount of purified water.

Thus, the hydrochloride addition salt of besifloxacin was never melted in the composition. Note that the melting point of the hydrochloride addition salt of besifloxacin is about 321-322° C.

The batch was sterilized at 122-126° C. for 38-45 minutes with continuous stirrer/scrapper mixing at about 40 rpm, then cooled to 20-30° C. with continuous mixing at 20-40 rpm.

An amount of water equal to 5 percent of the final desired batch weight was added to a clean, suitably sized stainless steel vessel equipped with a portable mixer operating at 300-600 rpm. The temperature was adjusted to 20-30° C.

An amount of benzalkonium chloride ("BAK") equal to about 0.1 percent of the final desired batch weight was added to the water while mixing continued until all of the BAK was dissolved.

The BAK solution was filtered through a sterilized 0.22 µm filter into the aseptic vessel containing the sterilized bulk suspension. When the transfer was complete, mixing continued with the stirrer/scrapper at 20-40 rpm.

Purified water was added aseptically to final batch weight at 20-30° C. Mixing continued with the stirrer/scrapper at 35-40 rpm and the homogenizer at not more than 200 rpm for 15-30 minutes.

Samples of the final suspension were packaged in individual sterilized bottles and labeled.

EXAMPLE 2

Preparing a Suspension Comprising Particles of Dexamethasone

The procedure of Example 1 is carried out for the preparation of a suspension comprising particles of dexamethasone. The solubility of dexamethasone in water is about 0.1 mg/mL at 25° C. Amounts of various ingredients may be varied to achieve the desired composition. In this example, dexamethasone phosphate disodium salt (soluble in water) is substituted for the hydrogen chloride addition salt of besifloxacin. Another carboxy-containing vinyl polymer, such as Carbopol® 934, may be substituted for Polycarbophil. Such a suspension can be used to treat inflammation.

EXAMPLE 3

Preparing a Suspension Comprising Particles of Azithromycin

The procedure of Example 1 is carried out for the preparation of a suspension comprising particles of azithromycin. The solubility of azithromycin in water is about 0.5 mg/mL. Amounts of various ingredients may be varied to achieve the desired composition. In this example, azithromycin dihydrate (solubility of about 39 mg/mL in water at 37° C.) is substituted for the hydrogen chloride addition salt of besifloxacin. Another carboxy-containing vinyl polymer, such as Pemulen™ TR-1, may be substituted for Polycarbophil. Such a suspension can be used to treat bacterial infection.

EXAMPLE 4

Preparing a Suspension Comprising Particles of Moxifloxacin

The procedure of Example 1 is carried out for the preparation of a suspension comprising particles of moxifloxacin. The solubility of moxifloxacin in water is estimated to be about 0.17 mg/mL. Amounts of various ingredients may be varied to achieve the desired composition. In this example, moxifloxacin hydrogen chloride addition salt (solubility in water of about 21 mg/mL) is substituted for the hydrogen chloride addition salt of besifloxacin. Another carboxy-containing vinyl polymer, such as Carbopol® 934, may be substituted for Polycarbophil. Such a suspension can be used to treat bacterial infection.

EXAMPLE 5

Preparing a Suspension Comprising Particles of Diclofenac

The procedure of Example 1 is carried out for the preparation of a suspension comprising particles of diclofenac. The solubility of diclofenac in water is estimated to be about 0.002 mg/mL. Amounts of various ingredients may be varied to achieve the desired composition. In this example, diclofenac sodium salt (solubility in water of about 50 mg/mL) is substituted for the hydrogen chloride addition salt of besifloxacin. Another carboxy-containing vinyl polymer, such as Carbopol® 940, may be substituted for Polycarbophil. As a variation of the method, the step of addition of BAK preservative may be eliminated in a preparation of the suspension that is packaged into unit doses for single uses. Such a suspension can be used to treat inflammation.

A suspension prepared by a method of the present invention, containing an API may find uses in the treatment of various disorders, such as infection, inflammation, etc., depending on the type of API that is contained therein. For example, a suspension containing besifloxacin, as disclosed above, can be used to treat ocular bacterial infection by administering one or two drops in the affected eye one or two times daily (or more often as directed by a medical practitioner) for several days until the infection is resolved.

The suspensions prepared by a method of the present invention show excellent physical and chemical stability. Table 1 shows analyses of samples taken at different depths of the vessel after 5 days of holding, indicating the suspension was stable without any settling of API particles.

TABLE 1

Physical and Chemical Analyses Confirming Stability of the Suspension

| Hold time | | Besifloxacin HCl (% label) | pH | Osmolality (mOsm/kg) | Viscosity (cps) | BAK (% label) | EDTA (% label) |
|---|---|---|---|---|---|---|---|
| day of preparation | Top | 102.4 | 6.3 | 285 | 1308 | 97.8 | 100.8 |
| | Middle | 101.3 | 6.4 | 283 | | 98.0 | 100.2 |
| | Bottom | 101.5 | 6.4 | 283 | | 97.7 | 100.0 |
| 5 days after preparation | Top | 102.4 | 6.4 | 285 | 1282 | 98.0 | 100.9 |
| | Middle | 102.0 | 6.4 | 285 | | 97.4 | 99.5 |
| | Bottom | 102.2 | 6.4 | 284 | | 97.4 | 100.3 |

Other studies were also conducted to evaluate the stability of suspensions prepared by a method of the present invention. In one study, four bottles from each of three manufactured lots (two lots included the API of Formula IV and one lot did not include the API ("the placebo")) were removed from stability chambers, which were kept at 25° C./40% RH after storage in an upright orientation. Each of these samples had been stored at this condition for more than two years, and the batches were beyond the nominal 24 month expiry period.

Procedure

Three bottles were taken from each of the two drag product lots. Each closed bottle was inverted (upside down) and shaken once before removing the cap with the bottle remaining in the inverted position. With the bottle in the inverted position, each bottle was gently squeezed to instill one drop into a tared vial (low-actinic glass) and the drop weight was recorded. In this manner, one drop of the suspension from each bottle was sampled into a separate vial every half hour for a total number of 10 drops per bottle. Between samplings, bottles were stored upright on the bench at ambient temperature.

After the first ten drops were expressed, the remaining contents were dispensed from each bottle continuously until the bottles were emptied. Every tenth drop was dispensed into a separate tared vial, and the drop weight recorded. All other drops were dispensed into a single vial and the total weight of these drops recorded to allow determination of an average drop weight from each bottle.

Each of the first 10 drops for each lot was assayed for each bottle. The next drop and each tenth drop after that, was assayed until the bottle was emptied. Each bottle contained an average of approximately 130 drops of drug product, which allowed for about 22 samples for assay per container.

The emptied bottles were cut in half and visually examined for the presence of any solid sediment or cohesive cakes.

For comparison, the fourth bottle from each lot was assayed directly from open containers that were completely mixed and homogenized. An assay value was obtained from an average of six samples.

The drug content of single drops was determined by spectrophotometry after being dissolved in appropriate solvent. Drops were brought to room temperature if they had been refrigerated. The content was determined as follows:

A weighed drop of besifloxacin suspension was diluted with 20 ml of diluent (consisting of 42% acetonitrile and 58% aqueous solution of 11 mM phosphoric acid and 0.38% sodium dodecyl sulfate). The absorbance of this sample preparation was measured at 298 nm. The placebo was used to adjust any blank contribution of excipients, although the placebo absorbance was low enough (Avg. 0.006 OD) that any contribution was relatively insignificant, since the absorbance of a sample was typically about 0.500 OD. Duplicate standards of Besifloxacin HCl reference standard were employed at nominal concentrations of 8.0 and 12.0 micrograms/mL.

Calculations and Data Analysis

The data from this study was plotted by recording delivered dose in micrograms as a function of sequence number for each weighed drop (9). The mean and standard deviation were calculated and compared to product sampled directly from the whole (mixed, homogeneous) container. The coefficient of determination was calculated between delivered dose of besifloxacin and drop weight. Results were calculated utilizing Microsoft Excel 2002 and Molecular Devices SpectraMax Plus 384 utilizing Softmax Pro v. 4.8. All statistical evaluations were made at the p=0.05 level.

Results and Discussion

Figure 2:
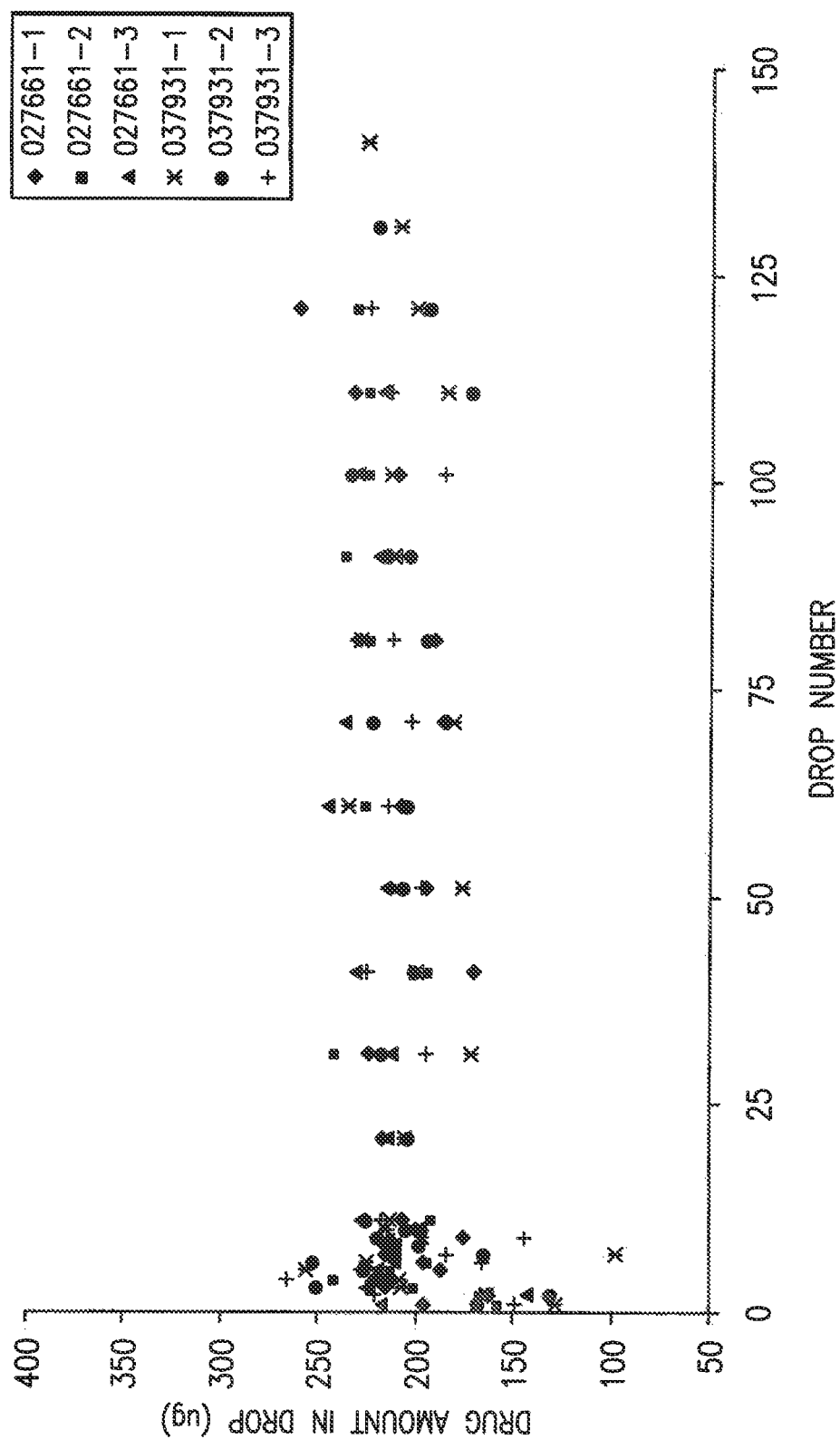
FIG. 2 shows the consistency of drug amounts in individual drops of a besifloxacin suspension produced by a method of the present invention, indicating that the particles remained suspended over a long storage time.
Figure 3:
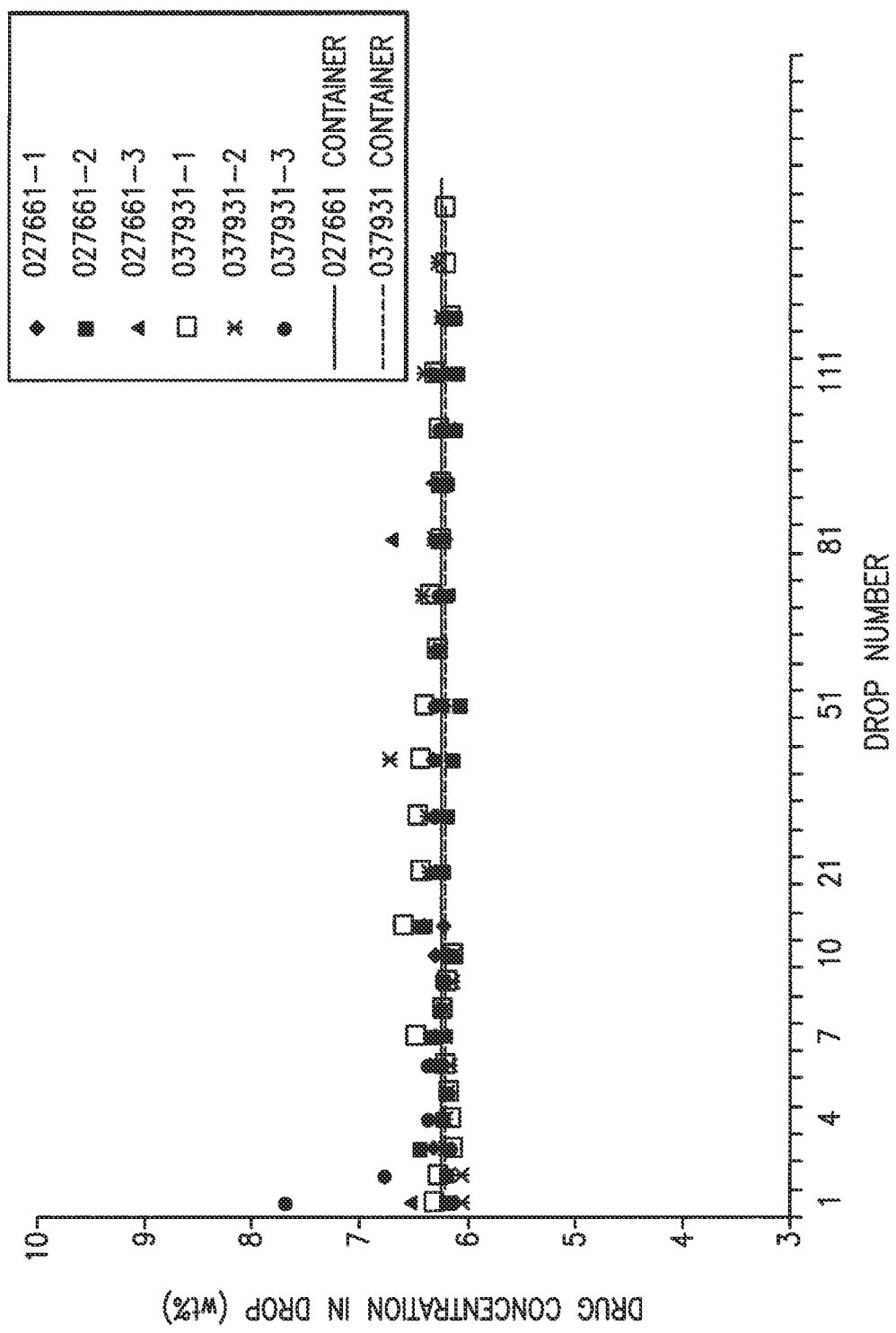
FIG. 3 shows the consistency of drug concentrations in individual drops of a besifloxacin suspension produced by a method of the present invention, indicating that the particles remained suspended over a long storage time.

Results for weight, drug content and potency of single drops covering the course of dispensing were collected and plotted in FIGS. 1-3. Results for drop weight collected from both tips were compared and found to be statistically equivalent and the variability was small (FIG. 1). The average drop weight was not statistically different from the average drop weight from studies performed two or more years prior using different lots of material. Although not definitive, this would suggest that there is no significant change over the 24-month shelf life.

Results for drug content of single drops covering the course of dispensing are plotted in FIG. 2. A total of 134 samples (21-24 drops per bottle) were assayed and the coefficient of determination ($r^2$) between dose and drop weight for all samples was greater than 0.95. This strong correlation indicated that the majority of dose variability was attributed to drop weight.

The potency determined from thorough mixing and sampling of the whole container was found to be within the specification requirements, even though the product was beyond the 24-month nominal shelf life.

Drop concentrations were plotted for each container (FIG. 3) and compared to the concentrations obtained for mixed, homogeneous samples, which are represented by the horizontal line. The difference between mean drop concentrations and container potency was small (<2%). Only five of the 134 individual drops examined (i.e. approximately 3.7%), were outside of the range of +/−5% of the concentration of the average bulk product. There were no sustained statistically significant trends (i.e., slope) of increasing or decreasing concentration or dose in any of the data sets.

These results demonstrate that the mixing of whole containers did not afford any significantly difference in average drug content relative to drops dispensed with a single shake via the clinical instructions. Our data demonstrates that the besifloxacin suspension, using the package with an inverted tip design, delivers the expected dose when the clinical instructions are followed.

CONCLUSIONS

The data from this study showed that the drug concentration of the drops delivered through bottle tips was typically very representative of the concentration of homogenized bulk product sampled without dispensing through the tip. The average means of drug potency delivered per drop were found to be in excellent agreement between the lots despite the different tins and no significant difference in drug potency was seen. Dose was essentially dependent on drop weight. Clinical dosing instructions, using the single shake before delivery of drops, provided sufficient mixing and dispersion to deliver the expected dose even after the individual bottles sat undisturbed for 24 months. Visual examination of each bottle demonstrated no drug particle sedimentation. Chemical and physical data confirmed no sign of settling or resuspendability issues.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A process for producing a pharmaceutical suspension that comprises an active pharmaceutical ingredient ("API") having low solubility, the process comprising:
    (a) preparing a first solution comprising a carboxy-containing vinyl polymer and water, said first solution having an acidic pH;
    (b) adjusting said pH of said first solution to, and maintaining said pH at, 6.5-6.7;
    (c) adjusting a temperature of said first solution to, and maintaining said temperature at, 20-30° C.;
    (d) adding a compound of the API to said first solution under conditions of high-shear mixing for a time from about 5 minutes to about 5 hours, said compound of the API being soluble in water, thereby producing a suspension of particles of said API in a composition comprising said carboxy-containing vinyl polymer;
    (e) adjusting a pH of said suspension to, and maintaining said pH at, 6.5-6.7; and
    (f) adjusting a temperature of said suspension to, and maintaining said temperature at, 20-30° C. to produce said pharmaceutical suspension;
    wherein said API is a quinolone, said compound is added in amount sufficient to yield a concentration of said API in said suspension that is higher than a solubility of said API in water; said compound is a salt, a hydrate, or a solvate of said API; and said compound is added in step (d) as a neat, solid material.

2. The process of claim 1, wherein the carboxy-containing vinyl polymer comprises a crosslinked polyacrylic add polymer.

3. The process of claim 1, wherein the crosslinked polyacrylic add polymer comprises polycarbophil.

4. The process of claim 1, wherein the carboxy-containing polymer is present at an amount of 0.01 to about 10 percent by weight of the final suspension.

5. The process of claim 1, wherein the particles of said API in said suspension have a mean particle diameter in the range from about 1 to about 4 µm, and a $D_{90}$ in the range from about 3 to about 7 µm.

6. The process of claim 5, wherein the suspension has a viscosity in the range from about 500 to about 3000 cp (or mPa·s).

7. The process of claim 1, wherein the conditions of high-shear mixing are effected by a mixing implement at a rotational speed in the range from about 500 to about 2000 rpm.

8. The process of claim 7, wherein the rotational speed is in the range from about 1000 to about 1600 rpm.

9. The process of claim 1; wherein the carboxy-containing polymer comprises a crosslinked polyacrylic acid polymer, the high-shear mixing conditions are effected by a mixing implement operating at about 500-2000 rpm, and the particles have a mean diameter in the range from about 1 to about 4 μm, and a $D_{90}$ in the range from about 3 to about 7 μm.

* * * * *